(12) United States Patent
Jin

(10) Patent No.: US 8,747,831 B2
(45) Date of Patent: Jun. 10, 2014

(54) METHOD AND ANTIBACTERIAL/ANTIMICROBIAL COMPOSITIONS IN DENTAL COMPOSITIONS

(75) Inventor: Xiaoming Jin, Middletown, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/530,248

(22) Filed: Jun. 22, 2012

(65) Prior Publication Data
US 2012/0328553 A1    Dec. 27, 2012

Related U.S. Application Data

(60) Provisional application No. 61/499,910, filed on Jun. 22, 2011.

(51) Int. Cl.
*A61K 31/74*    (2006.01)

(52) U.S. Cl.
USPC ........................................................ 424/78.08

(58) Field of Classification Search
None
See application file for complete search history.

(56) References Cited

U.S. PATENT DOCUMENTS

| | | |
|---|---|---|
| 5,494,987 A | 2/1996 | Imazato |
| 6,710,181 B2 | 3/2004 | Kumagai et al. |
| 7,094,845 B2 | 8/2006 | Kumagai et al. |
| 7,553,881 B2 | 6/2009 | Salz et al. |
| 2003/0064102 A1 | 4/2003 | Nakatsuka |
| 2008/0070966 A1 | 3/2008 | Elder et al. |
| 2010/0234549 A1 | 9/2010 | Jin et al. |
| 2010/0256242 A1 | 10/2010 | Antonucci et al. |

FOREIGN PATENT DOCUMENTS

| | | |
|---|---|---|
| DE | 102005023799 A1 | 11/2006 |
| WO | 2011087621 A2 | 7/2011 |
| WO | WO 2011087621 A2 * | 7/2011 |

OTHER PUBLICATIONS

International Search Report, Application No. 2012/043667, Published Jun. 22, 2012.
International Written Opinion, Application No. 2012/043667, Published Jun. 22, 2012.

* cited by examiner

*Primary Examiner* — Paul Dickinson
(74) *Attorney, Agent, or Firm* — Leana Levin; Douglas J. Hura; David A. Zdurne

(57) ABSTRACT

Disclosed herein is a composition and method of making a polymerizable antibacterial/antimicrobial resin and using such a bioactive resin in formulated dental compositions.

3 Claims, 14 Drawing Sheets

| Microorganism | Sample | Contact Time | CFU / Coupon | R Value |
|---|---|---|---|---|
| S. mutans ATCC 26175 | Control | Time Zero | 8.10E+05 | N/A |
| | | 24 Hours | 3.30E+03 | |
| | Treated | Time Zero | 7.60E+05 | >2.82 |
| | | 24 Hours | <5 | |

METHOD AND ANTIBACTERIAL/ANTIMICROBIAL COMPOSITIONS IN DENTAL COMPOSITIONS

This application claims priority U.S. Provisional Patent Application No. 61/499,910, files Jun. 22, 2011.

FIELD OF USE

Disclosed herein is a composition and method of making a polymerizable antibacterial/antimicrobial resin and using such a bioactive resin in formulated dental compositions.

BACKGROUND

Dental caries are associated with the bacterial contained in dental biofilm. Dental biofilm is complex, with a well-organized structure. Up to 500 bacterial species have been identified in dental biofilm. For oral and systemic health, the dental biofilm needs to be regularly and meticulously removed. Removal and reduction of biofilm can be by mechanical means or mechanical and chemical means. There have been increasing efforts to inhibit the development of biofilm. It is known prior to the development of dental biofilm, the salivary or acquired pellicle forms. This occurs through the adsorption of protein from saliva onto the clean tooth surface. Acquired pellicle formation provides oral bacterial with biding sites, resulting in bacterial adhesion, the first step in the formation of dental biofilm. Therefore, surface modification should inhibit the development of the acquired pellicle and dental biofilm.

In restorative dentistry, secondary caries are well known, which often occurs at the interface between the restoration and the cavity preparation as a result of demineralization of tooth structure due to the dental plaque formation by acid-producing bacteria such as *Streptococcus mutans* (*S. mutans*) in presence of fermentable carbohydrates. Thus dental compositions with antibacterial/antimicrobial effect were formulated by incorporation of a variety of antibacterial/antimicrobial agents, such as chlorhexidine, silver ions, and fluoride. Although such low molecular organic compounds demonstrated immediate effectiveness, there are issues related to their long-term effectiveness, potential toxicity and impact to the mechanical strength of the formulated dental composition due to the leachability. On the other hand, solid antibacterial/antimicrobial agents such as silver nanoparticles and polymeric QAS nanoparticles were also developed to address those issues associated with the low molecular weight of antibacterial/antimicrobial agents. There are issues like color stability and optical opacity and mechanical strength. Recently polymerizable antibacterial/antimicrobial resins were developed but their effectiveness varied and most of them demonstrated negative impact on mechanical property of the formulated dental composition.

U.S. Pat. No. 5,494,987 disclosed antimicrobial polymerizable compositions having an ethylenically unsaturated monomer with antimicrobial activity for dental application composed of quaternary ammonium dodecylpyridinium (MDPB).

U.S. Publication No. 2010/0256242 disclosed a polymerizable biomedical composition that includes a quaternary ammonium group bonded at its quaternary sites.

U.S. Pat. Nos. 6,710,181 and 7,094,845 disclosed an imidazole-based silane and monocarboxylic acid salt for improving adhesion between resins and metal or glass.

U.S. Pat. No. 7,553,881 disclosed dental compositions based on polymerizable macromers based on quaternary ammonium salts for antimicrobial effect.

Thus there is strong need to highly effective polymerizable antibacterial resin that is capable to offer a balanced antibacterial effectiveness and excellent mechanical property without severe cytotoxicity. In this invention, a method and composition of polymerizable antibacterial/antimicrobial resins is disclosed and high performance dental compositions are formulated from such novel bioactive resins.

SUMMARY

Disclosed herein is a composition and method of making and using such a composition in dental restorations. The composition disclosed herein includes novel polymerizable resins. More specifically, the composition disclosed herein is related to a method of preparing such polymerizable resins that contains multiple imidazolium groups and multiple radically polymerizable groups as shown in the following formula:

$$(A-X)_n—Z—(Y—BQR)_m$$

A: polymerizable moiety like methacrylate, acrylate, epoxy, vinylether, etc; n=1, 2, 3, 4 . . . .

B: substituted imidazole moiety like imidazole, methylimidazole, etc, m=1, 2, 3, 4, . . . .

R: a hydrogen atom or an alkyl group having 1-22 carbon atoms

Q: counter ion groups such as halogen atom, chlorine, bromine, iodine, etc

X, Y: equal or different, ether, ester, amide, imide, direct link, alkyl, aromatic, etc, Z: alkyl, aromatic, etc.

Furthermore, formulated dental compositions, including composite or cements, from this invented polyimidazolium resin are able to offer balanced antibacterial effectiveness and mechanical property without causing any severe cytotoxicity. Such resins may be formulated with conventional resins to provide an improved adhesive to hard tissues in a prepared tooth cavity.

DETAILED DESCRIPTION

Figure 1:
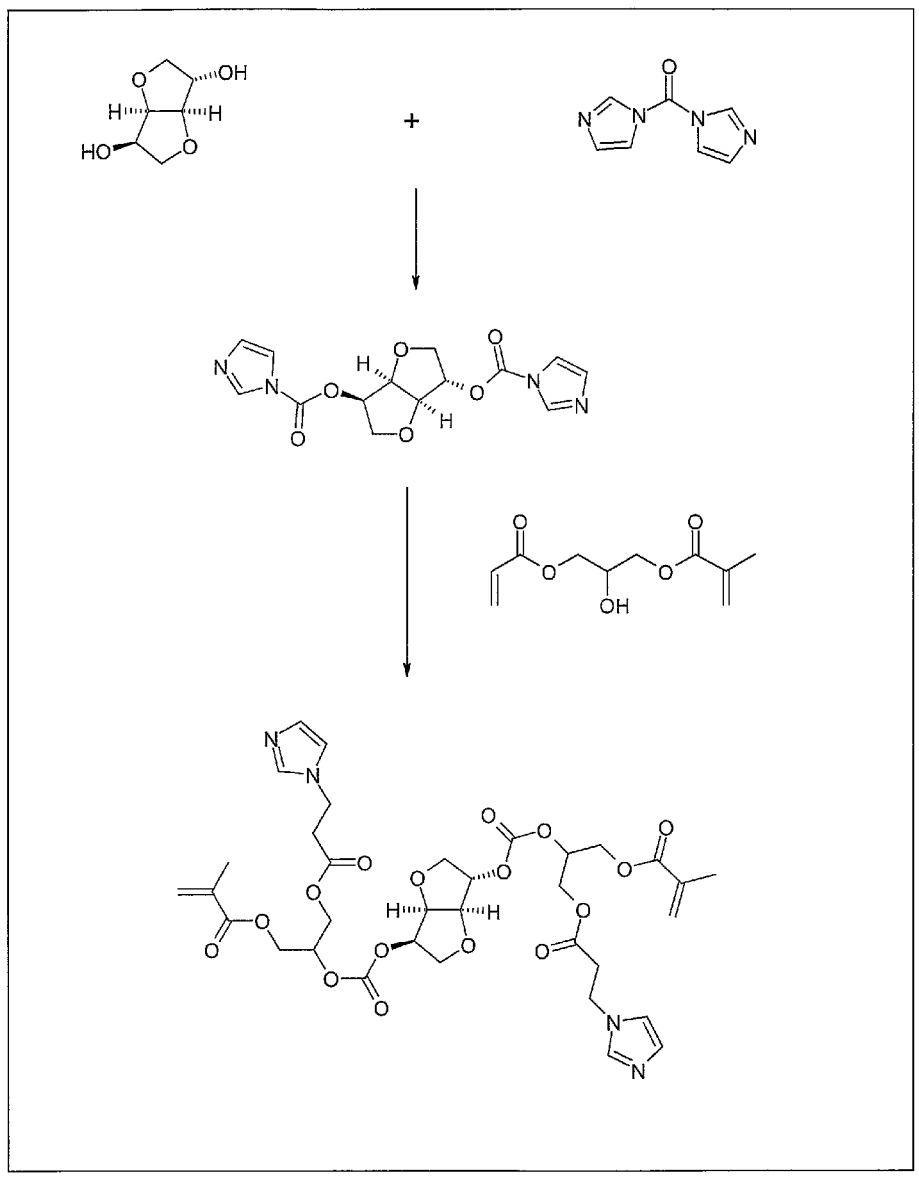
FIG. 1 depicts isosorbide-based bisimidazole-dimethacrylate resins.

During the attempt to prepare a carbonate-based polymerizable resin (FIG. 1) by using an acrylate-methacrylate resin (AMAHP) and 1,1-carbonyl-diimidazole (CDI), it was surprisingly discovered that a chemically bonded imidazole resin was formed exclusively in the resulting resin. It has been elucidated that the formation of the imidazole resin was the result of a Michael adduct between the acrylate group in AMAHP and the CDI in-situ generated by-product (imidazole) in the absence of any catalysts. The imidazole was found to react exclusively toward the acrylate group. Thus a variety of polymethacrylated resins containing at least one polyimidazole moiety could be readily prepared by proper hybrid acrylate-methacrylate resins or even polyacrylate resins with proper control of the conversion of the imidazole addition. Therefore, this is an effective method to incorporate an imidazole moiety into a polymerizable resin as novel functional resins for acid-free adhesive resins. Furthermore, such polymerizable imidazole-containing resins may be further chemically modified by reaction with a variety of halogenated alkyls to form polymerizable resins with ionic moiety of imidazolium, which may be new class of polymerizable ionic liquid resins.

Figure 2:
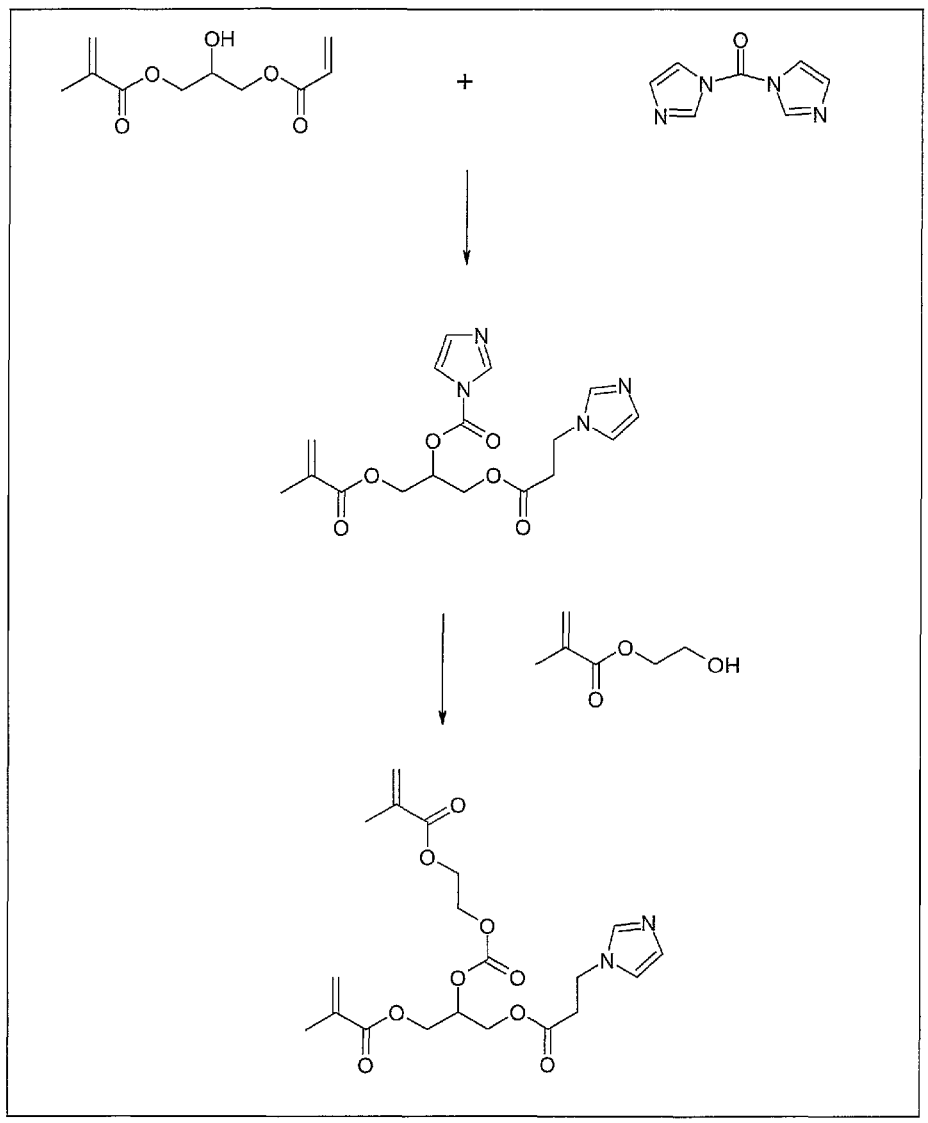
FIG. 2 depicts a CDI-based reaction pathway to monoimidazole-dimethacrylate resin.
Figure 3:
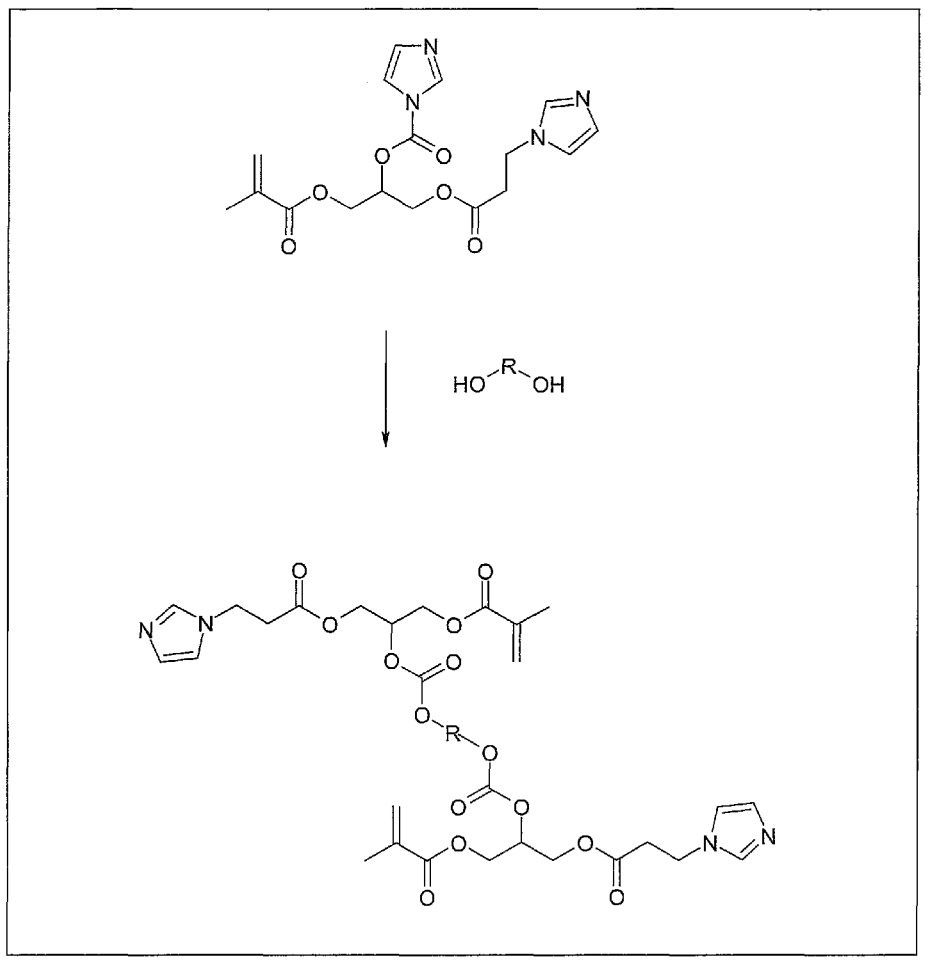
FIG. 3 depicts CDI-based reaction pathways to bisimidazole-dimethacrylate resins.
Figure 4:
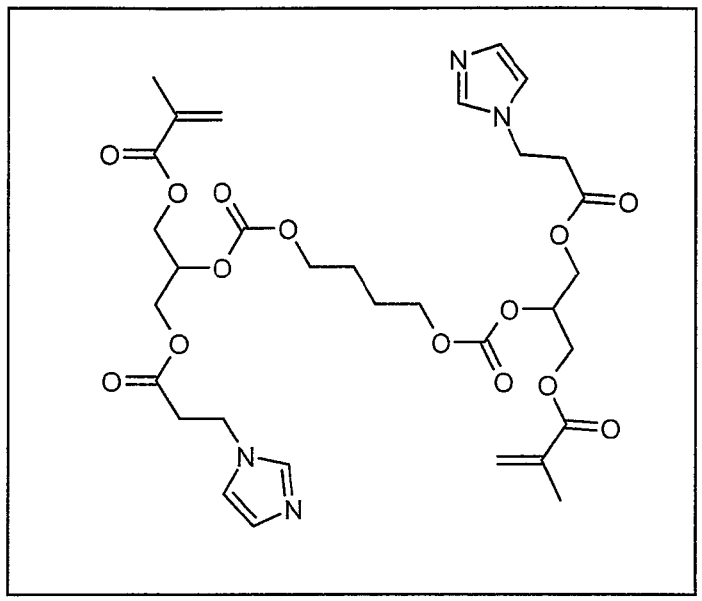
FIG. 4 depicts a butanediol-based bisimidazole-dimethacrylate resin.
Figure 5A:
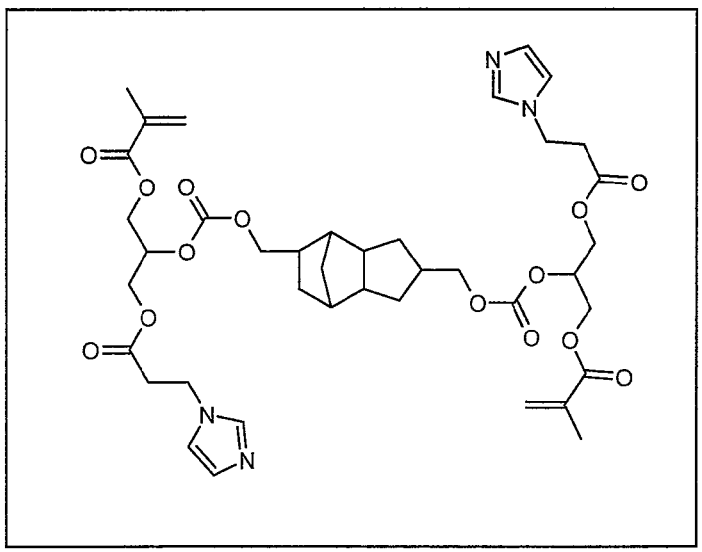
FIG. 5a depicts a TCDC-based bisimidazole-dimethacrylate resin.
Figure 5B:
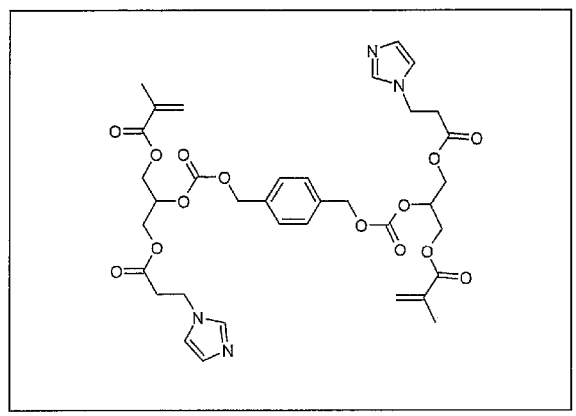
FIG. 5b depicts a paraXylenediol-based bisimidazole-dinnethacrylate resin.

Accordingly from such a reaction platform, other derivatives may be readily prepared as illustrated in FIGS. 2 through 5: a variety of polymethacrylate resins with polyimidazoles are able to be prepared via the precursor as showed in FIGS. 2 and 3 by coupling with different mono, di, tri, or polyols or polyamines.

Figure 6:
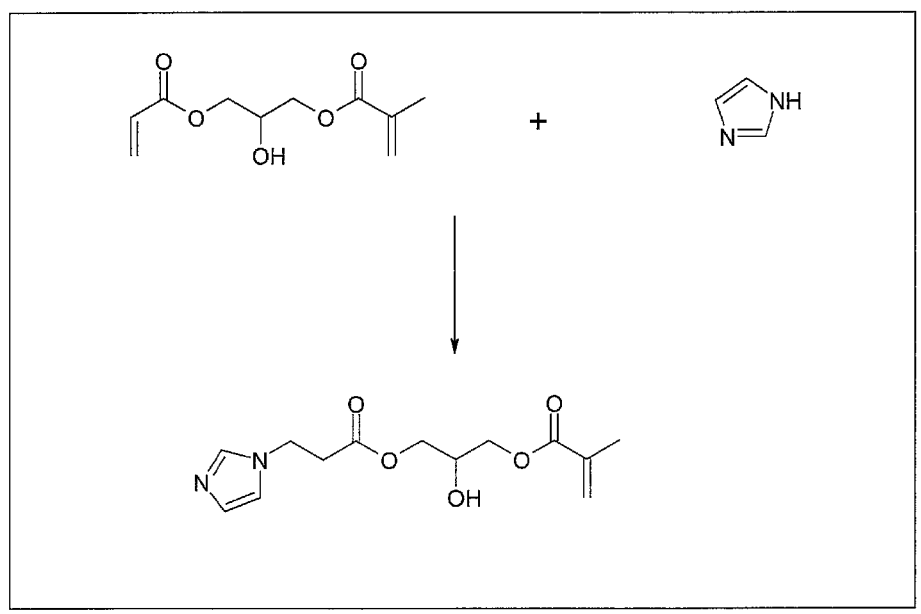
FIG. 6 depicts an imidazole-based reaction pathway to monoimidazole-monomethacrylate resin.
Figure 7:
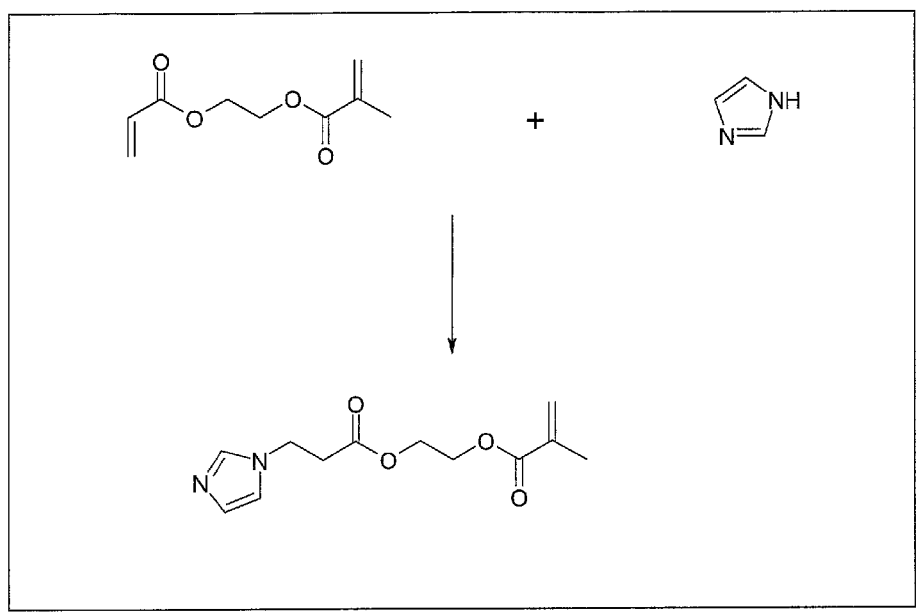
FIG. 7 depicts an imidazole-based reaction pathway to monoimidazole-monomethacrylate resin.
Figure 8:
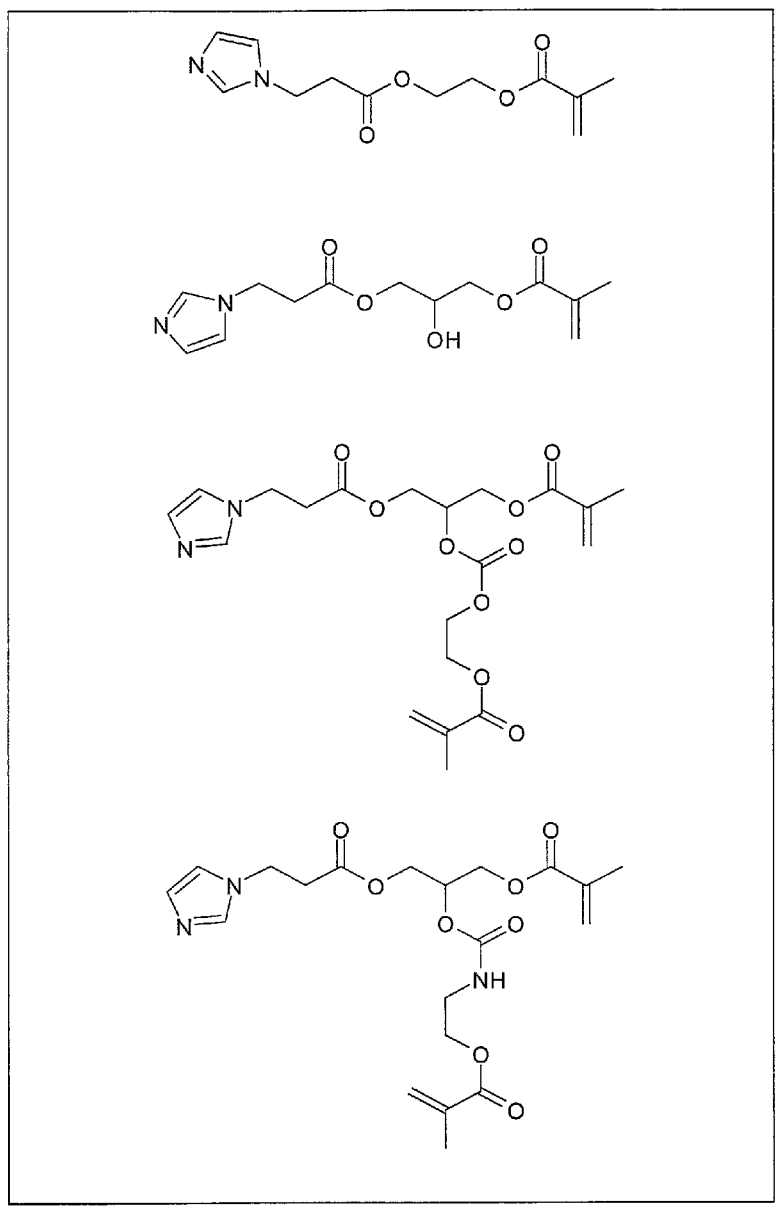
FIG. 8 depicts typical monoimidazole resins.
Figure 9:
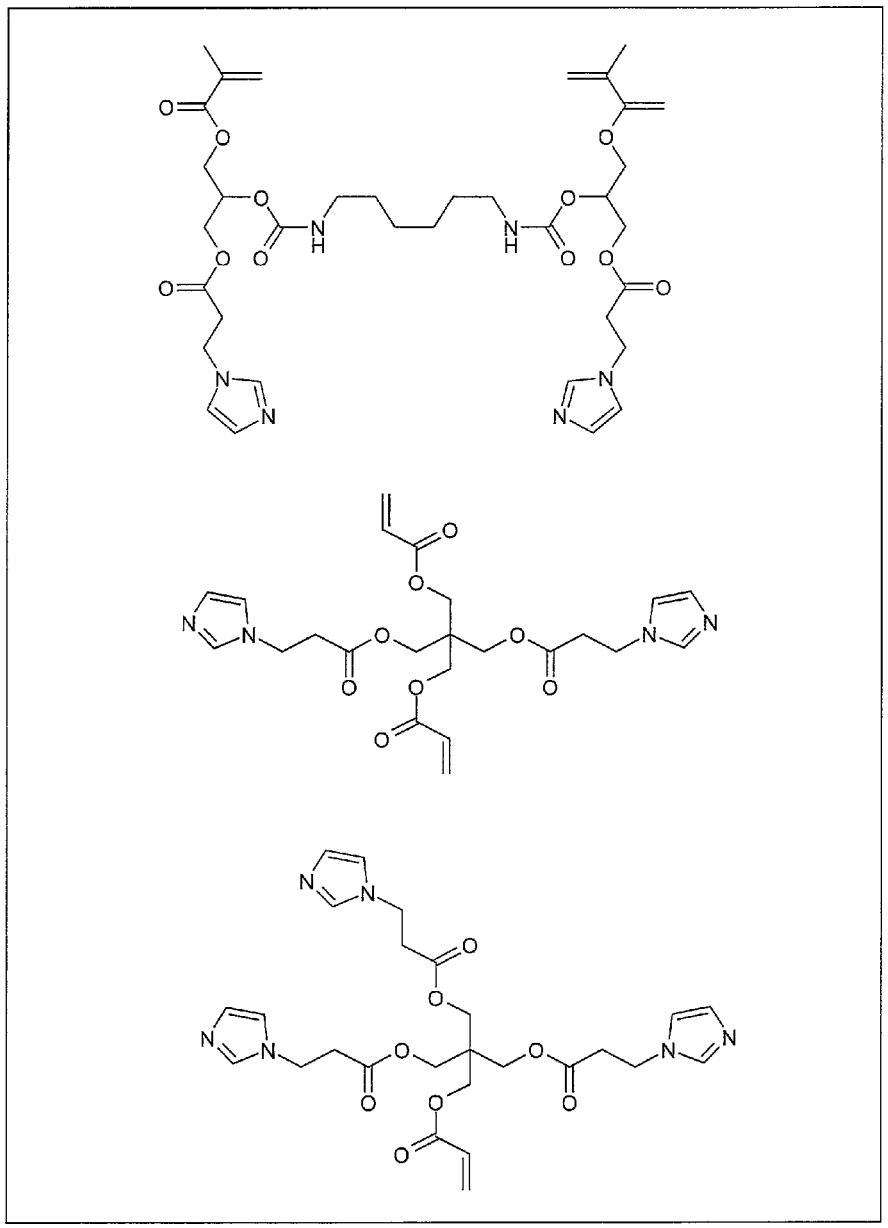
FIG. 9 depicts other polyimidazole(meth)acrylate resins.
Figure 10:
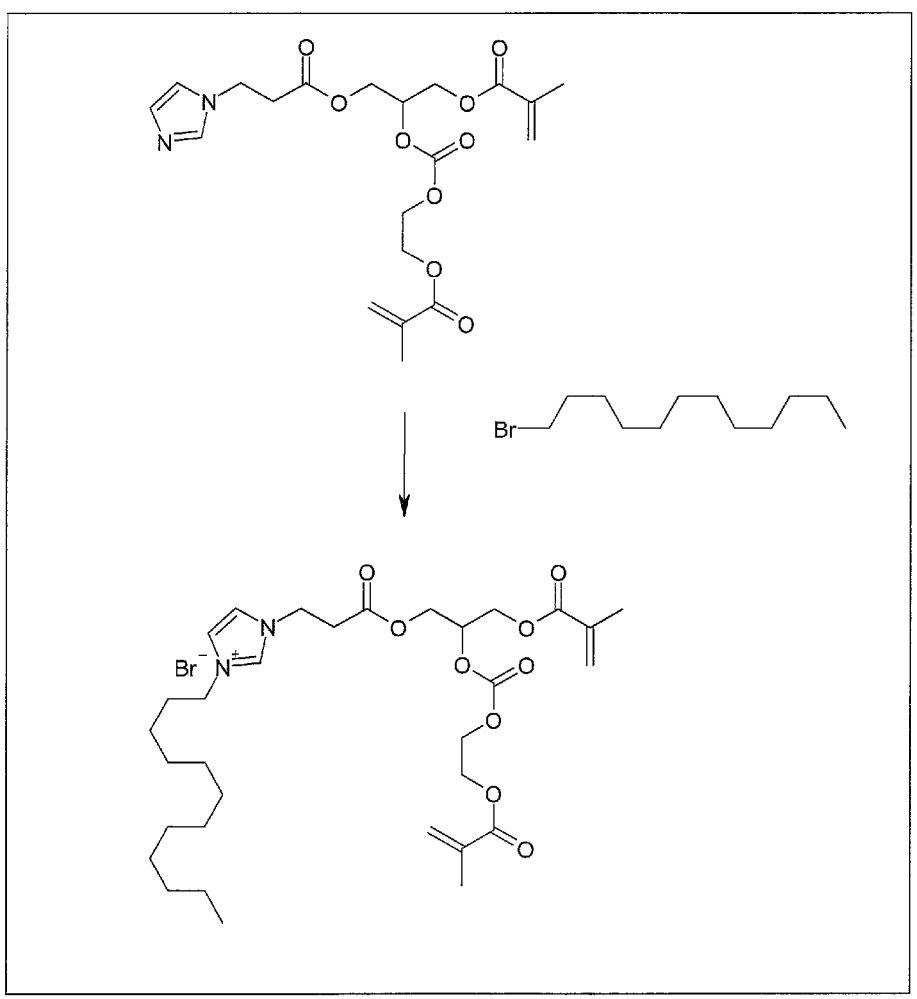
FIG. 10 depicts a reaction of 3-dodecanylimidazoliumbromide-dimethacrylate resin.
Figure 11:
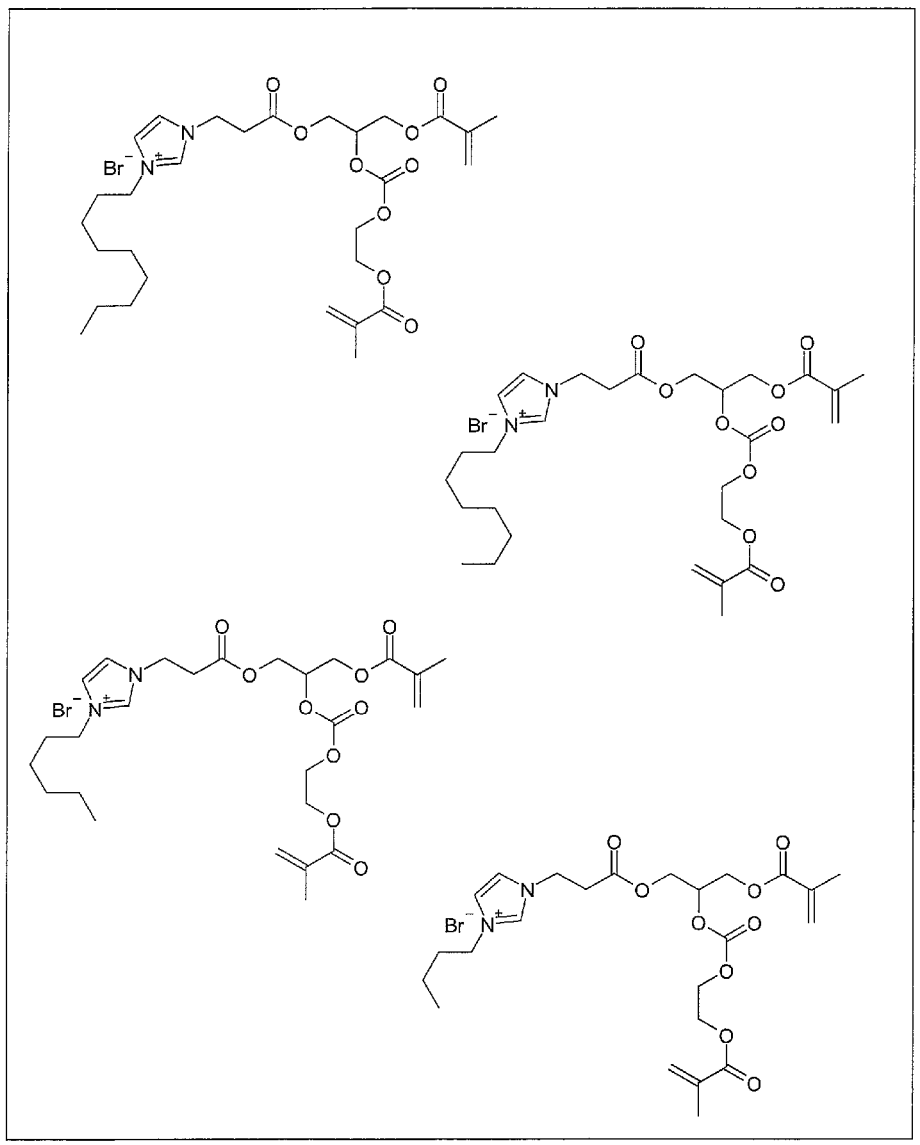
FIG. 11 depicts typical alkylimidazoliumbromide-dimethacrylate resins.
Figure 12:
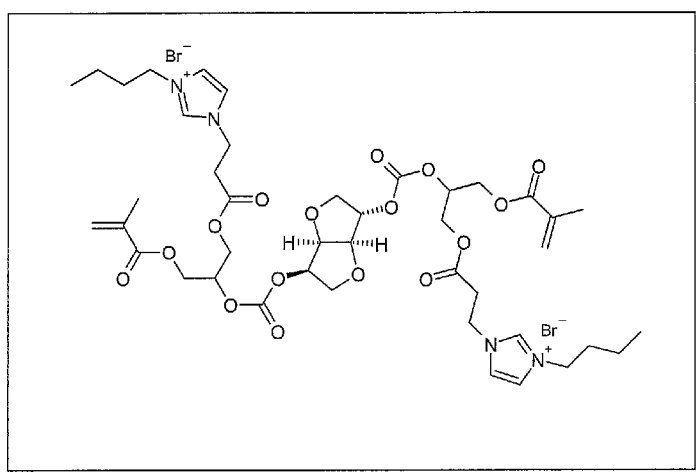
FIG. 12 depicts an isosorbide-based bis(3-butylimidazoliumbromide)-dimethacrylate resin.
Figure 13:
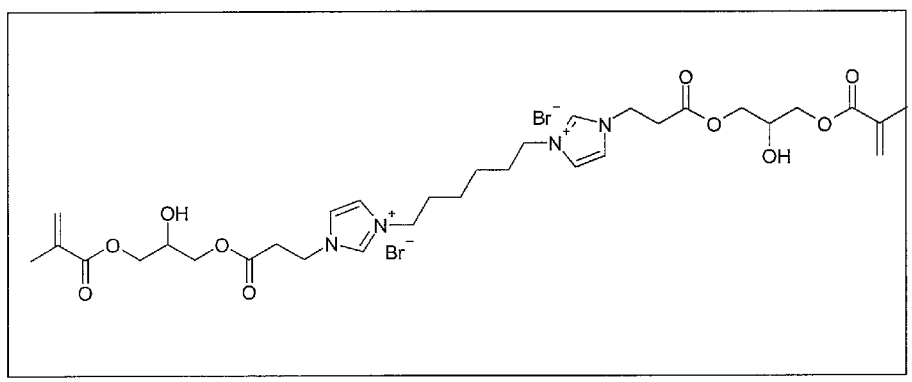
FIG. 13 depicts a 1,6-hexane-bisimidazoliumbromide-dimethacrylate resin.
Figure 14:
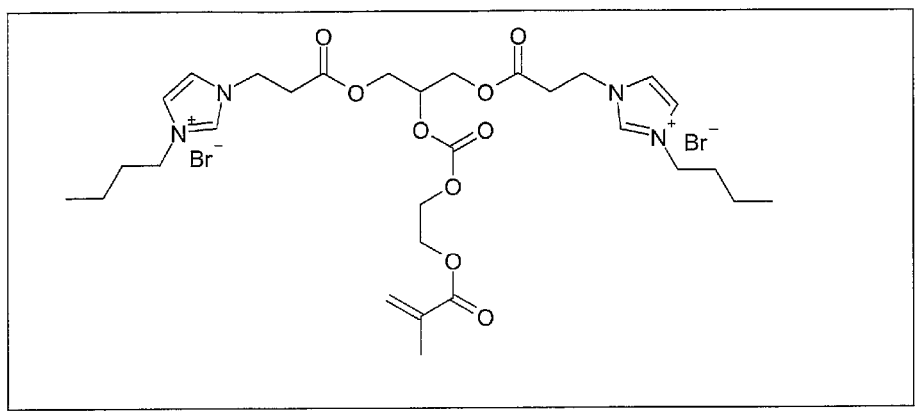
FIG. 14 depicts a bis(3-butylimidazoliumbromide)-bisacrylate resin.
Figure 15:
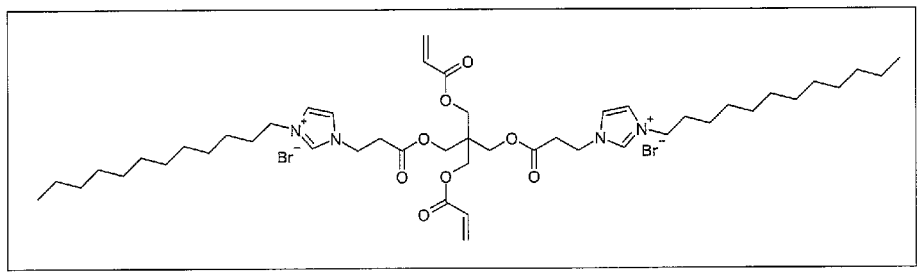
FIG. 15 depicts a bis(3-dodecanylimidazoliumbromide)-bisacrylate resin.

Further, in order to streamline the process of making such imidazole-based polymerizable resins for use in making imidazolium-based polymerizable resins, a facile process based on imidazole and acrylated resins were investigated as illustrated in FIGS. 6 and 7. Thus a variety of imidazole-based polymerizable resins are able to be prepared, as shown in FIGS. 8 and 9.

Furthermore, as illustrated in FIGS. 10 through 15, a variety of imidazolium-based polymerizable resins may be prepared from a wide range of imidazole-based polymerizable resins as discussed previously. The preferred imidazolium-based polymerizable resin contains at least one polymerizable group such as methacrylate or acrylate and at least one imidazolium moiety bearing linear long alkyl chain of C8-C14. The most preferred resin contains two methacrylate group and at least one imidazolium moiety bearing a C12 linear alkyl chain.

Figure 17:
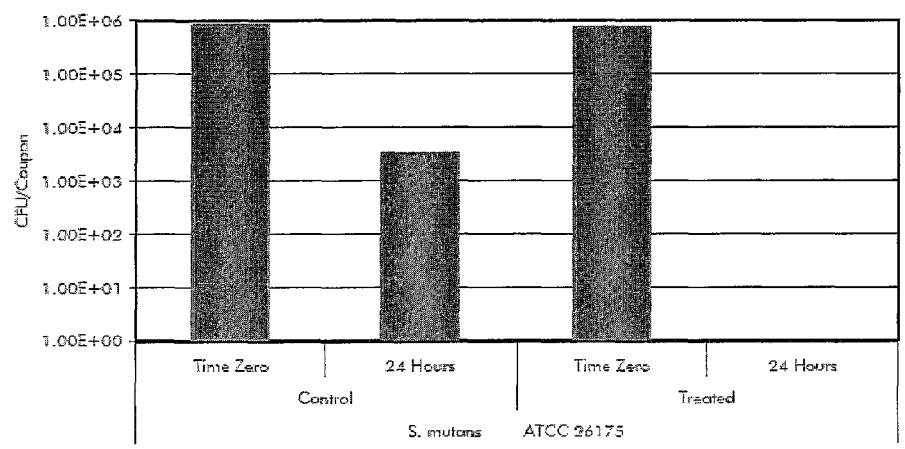
FIG. 17 depicts the antibacterial effectiveness of polymerizale antibacterial resin against S. mutans.

Such imidazolium-based polymerizable resin was found highly effective in killing bacteria such as S. mutans as showed in FIG. 17. It was also demonstrated that such imidazolium-based polymerizable resins are also very effective in inhibiting MMP even at low concentration. Matrix metalloproteinases (MMP) bond to dentin and are thought to contribute to the progressive degradation of collagen fibrils in hybrid layers formed during dentin bonding. The dentin matrix contains MMP-2, MMP-8, MMP-9, and MMP-20. It is known that chlorhexdine (CHX) has broad anti-MMP activity in addition to antimicrobial activity. However, the long term anti-MMP activity for CHX is not effective, which has been attributed to possible leaching out of the CHX. It has been shown that cationic quaternary ammonium methacrylates (QAS) may exhibit dentin MMP inhibition comparable with that of CHX, but require higher concentrations.

Figure 18:
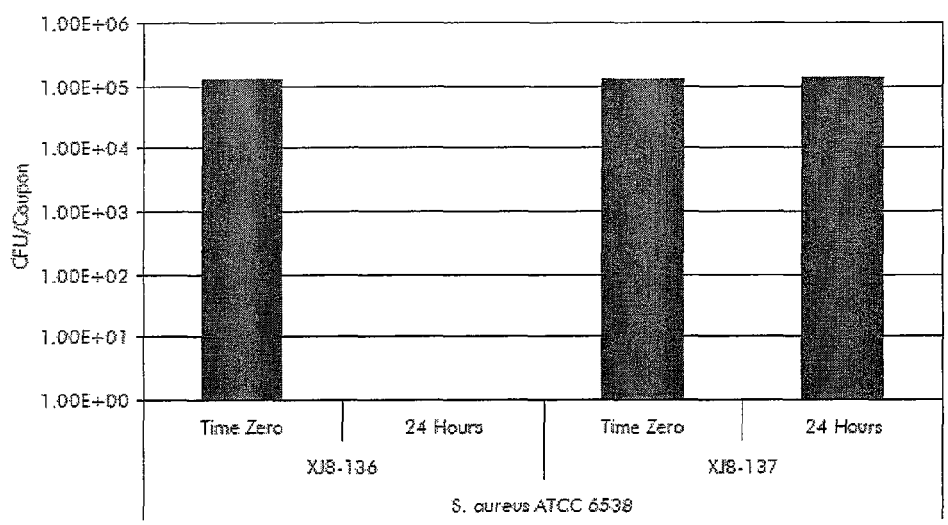
FIG. 18 depicts the antibacterial effectiveness of cured composite containing antibacterial resin against S. aureus.

Such effectiveness in killing bacteria for the imidazolium-based polymerizable resins were further demonstrated by the formulated dental composites as showed in Table V and FIG. 18. More importantly it was discovered that a low level loading (less than 1%, wt/wt) of such an imidazolium-based polymerizable resin may remain effective in killing bacteria as showed in Table VI. Furthermore, with optimized compositions not only highly effective antibacterial activity is achieved but also excellent mechanical properties were yielded as shown in Tables VII through XIV. The effectiveness in antibacterial properties of this novel polymerizable imidazolium resin offers another crucial benefit without causing severe cytotoxicity. Conventional QAS-based polymerizable resins, on the other hand, are less effective and high dose loading (up to 30%) is needed, which usually leads to decreases in mechanical property and increases cytotoxicity.

Obviously from the resin disclosed herein a variety of applications could be found as photopolymerizable dental products. Certainly, it can also be polymerized by heat, and/or redox initiation process. In addition, due to the nature of the imidazole moiety, it is also expected that the disclosed polymerizable resin can also find application in forming a complex with acidic resins or polymers, including PENTA, OEMA, methacrylic acid, polyacrylic acid or reactive acidic glass powders to form a soluble liquid resin, soft gel or hard gel structures or highly-crosslinked solids.

Disclosed herein is a composition and method of making and using such compositions in dental restorations. The composition disclosed herein includes novel polymerizable resins. More specifically, the composition disclosed herein is related to a method of preparing such polymerizable resins that contains multiple imidazole groups and multiple radically polymerizable groups as shown in the following formula:

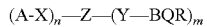

$(A-X)_n-Z-(Y-BQR)_m$

A: polymerizable moiety like methacrylate, acrylate, epoxy, vinylether, etc; n=1, 2, 3, 4 . . . .

B: substituted imidazole moiety like imidazole, methylimidazole, etc, m=1, 2, 3, 4, . . . .

R: a hydrogen atom or an alkyl group having 1-22 carbon atoms

Q: counter ion groups such as halogen atom, chlorine, bromine, iodine, etc

X, Y: equal or different, ether, ester, amide, imide, direct link, alkyl, aromatic, etc, Z: alkyl, aromatic, etc.

Dental composition disclosed herein may be composed of (1) the functional polymerizable resins contains imidazole group or imidazolium groups described herein in amount of from about 0.5 weight percent to about 99 weight percent of the dental composition, (2) conventional polymerizable resin in amounts of from about 10 weight percent to about 99 weight percent of the dental composition, (3) initiators and other additives in amounts of from about 0.001 weight percent to about 5.0 weight percent of the dental composition, (4)

a plurality of filler particles having a size of from about 10 nm to about 100 micron of the dental composition, and (5) an optional inert solvent in amounts not to exceed 1 weight percent of the dental composition.

HEMA and HPMA are typical monomethacrylate resins; BisGMA, TEGDMA, UDMA are typical conventional dimethacrylate resins, which are polymerizable/curable by heat, light and redox initiation processes. CQ and LTPO are typical photoinitaiors. Tertiary aromatic amines, such as EDAB, may be included as an accelerator for CQ-based photoinitiator. Other additives such as inhibitors, UV stabilizers or fluorescent agents may also be used. In addition, a variety of particles, polymeric, inorganic, organic particles may be incorporated to reinforce the mechanical properties, rheological properties and sometime biological functionalities.

The following abbreviations may be used:
BisGMA: 2,2-bis(4-(3-methacryloyloxy-2-hydroxypropoxy)-phenyl)propane
HEMA: 2-hydroxyethyl methacrylate
HPMA: 2-hydroxypropyl methacrylate
TEGDMA: triethylene glycol dimethacrylate
UDMA: di(methacryloxyethyl)trimethyl-1,6-hexaethylene-diurethane
BHT: butylhydroxytoluene
CQ; camphorquinone
LTPO: lucirin TPO/2,4,6-trimethylbenzoyldiphenylphosphine oxide
EDAB: 4-Ethyl dimethylaminobenzonate
AMAHP: 3-(acryloyloxy)-2-hydroxypropyl methacrylate
EGAMA: ethyleneglycol acrylate methacrylate
TCDC: 4,8-bis(hydroxymethyl)-tricyclo$[5,2,1,0^{2.6}]$
CDI: 1,1-carbonyl-diimidazole
SR295: pentaerythritol tetraacrylate

EXAMPLES

Example 1

Isosorbide-based Bisimidazole-dimethacrylate Resin (XJ8-9/FIG. 1) was prepared via a two-step process as described in the following: to a 1000 ml 3-nech round flask, 98.88 g of 1,1-carbonyl-diimidazole (CDI), 550 g of methylene dichloride and 43.9 g of isosorbide was charged and soon the system turned clear at room temperature. Then the crystal was developed as a result of imidazole formation. After 2 hrs reacting at RT, 131.1 g of 3-(acryloyloxy)-2-hydroxypropyl methacrylate (AMAHP), 40.0 g of potassium carbonate and 4.0 g of terabutylamoniumbromide was added. The reaction proceeded at room temperature for an additional 10-12 hrs prior to 200 ml of DI water being added to stop the reaction. The resulting solution was extracted several times with DI water to remove all of imidazole and catalysts. Then it was dried over magnesium sulfate overnight at RT prior to being filtrated. Solvent was removed via Rotovapor at 35-40° C. under vacuum. 240 g of liquid resin was collected with a yield of 89%.

Example 2

TCDC-based Bisimidazole-dimethacrylate Resin (XJ8-13/FIG. 5a) was prepared via a two-step process as described in the following: to a 1000 ml 3-nech round flask, 74.45 g of CDI, 400 ml of methylene dichloride and 98.36 g of AMAHP was charged and soon the system turned clear at room temperature. After 6 hrs reacting at RT, 45.0 g of 4,8-bis(hydroxymethyl)-tricyclo$[5,2,1,0^{2.6}]$(TCDC) and 40.0 g of potassium carbonate and 3.8 g of terabutylamoniumbromide was added. The reaction continued at room temperature for an additional 10-12 hrs prior to 250 ml of DI water being added to stop the reaction. The resulting solution was extracted several times with DI water to remove all of imidazole and catalysts. Then it was dried over magnesium sulfate overnight at RT prior to it being filtrated. The solvent was removed via Rotovapor at 35-40° C. under vacuum.

Example 3a

HEMA-based Monoimidazole-dimethacrylate Resin (XJ8-6/FIG. 2) was prepared via a two-step process as described in the following: to a 1000 ml 3-nech round flask, 81.8 g of CDI, 450 ml of methylene dichloride and 107.5 g of AMAHP was charged and soon the system turned clear at room temperature. After a 6 hrs reaction at RT, 66.5 g of 2-hydroxyethyl methacrylate (HEMA), 40.0 g of potassium carbonate and 4.0 g of terabutylamoniumbromide was added. The reaction continued at room temperature for an additional 10-12 hrs prior to 200 ml of DI water being added to stop the reaction. The resulting solution was extracted several times with DI water to remove all of the imidazole and catalysts. Then the solution was dried over magnesium sulfate overnight at RT prior to being filtrated. The solvent was removed via Rotovapor at 35-40° C. under vacuum.

Example 3b

HEMA-based Monoimidazole-dimethacrylate Resin (XJ8-48/FIG. 2) was prepared via a two-step process as described in the following: to a 1000 ml 3-nech round flask, 120.3 g of CDI and 200 ml of methylene dichloride were added. Then 159.3 g of AMAHP in 150 ml of methylene dichloride was charged and soon the system turned clear at room temperature. After an overnight reaction at RT, 100.1 g of HEMA, 40.0 g of potassium carbonate and 4.0 g of terabutylamoniumbromide were added. The reaction continued at room temperature for an additional 4 hrs prior to 200 ml of DI water being added to stop the reaction. The resulting solution was extracted several times with DI water to remove all of the imidazole and catalysts. Then the solution was dried over magnesium sulfate overnight at RT prior to being filtrated. The solvent was removed via Rotovapor at 35-40° C. under vacuum. 301 g of low viscosity liquid resin was collected.

Example 3c

AMAHP-based monosimidazole-methacrylate Resin (XJ8-111/FIG. 6) was prepared via a one-step solution process as described in the following: to a 2000 ml 3-neck flask, 800 ml of methylene dichloride, 161.1 g of AMAHP and 102.2 g of imidazole were charged. Soon the imidazole got dissolved and the clear solution was mixed at room temperature overnight prior to 200 ml of DI water being added to stop the reaction. The resulting solution was extracted several times with DI water to remove all of the excess imidazole and catalysts. Then the solution was dried over magnesium sulfate overnight at RT prior to being filtrated. The solvent was removed via Rotovapor at 35-40° C. under vacuum. 200 g of low viscosity liquid resin was collected, from which a reversible gel-like resin is formed once the temperature down to RT.

Example 3d

EGAMA-based monosimidazole-methacrylate Resin (XJ8-157/FIG. 7) was prepared via a one-step bulk process as described in the following: to a 500 ml 3-nech round flask, 184.5 g of ethyleneglycol acrylate methacrylate (EGAMA) and 69.3 g of imidazole were charged. This slurry was mixed at room temperature for 60 hrs. 250 g of low viscosity liquid resin was collected.

Example 4

HEMA-based Monoimidazoliumbromide-dimethacrylate Resin (XJ8-45/FIG. 10) was prepared by a one-step condensation reaction from the imidazole precursor prepared as described in Example 3b. To a 250 ml 3-neck round flask, 61.7 g of HEMA-based monoimidazole-dimethacrylate resins (XJ8-38) and 40.2 g of 1-bromododecane and 200 ml of methylene dichloride was charged. The reaction continued at 40° C. for 7 days. Added 135 grams of hexane to the system and it is immiscible. After separated the hexane solution part, the resin was dissolved in methylene dichloride and extracted with water for several times. The solvent was removed via Rotovapor at 35-40° C. under vacuum. 80 grams of clear liquid resin was collected, which had a viscosity of 140 Pa·s at 20° C.

Example 5

Isosorbide-based Bisimidazoliumbromide-dimethacrylate Resin (XJ8-31/FIG. 12) was prepared by a one-step solution reaction from the imidazole precursor prepared as described in Example 1. To a 500 ml 3-neck round flask, 42.4 g of Isosorbide-based bisimidazole-dimethacrylate resins (XJ8-9), 13.7 g of 1-bromobutane, 200 ml of methylene dichloride and 8.65 g of triethylene glycol dimethacrylate (TEGDMA) were charged. The reaction continued at 40° C. for 2 days. Finally 65 g of highly viscose liquid resin was collected. The RI of this resin is 1.5130.

Example 6

HEMA-based Monoimidazoliumbromide-dimethacrylate Resin (XJ8-40/FIG. 11) was prepared by a one-step condensation reaction from the imidazole precursor prepared as described in Example 3b. To a 250 ml 3-neck round flask, 21.92 g of HEMA-based monoimidazole-dimethacrylate resins (XJ8-38) and 8.22 g of 1-bromobutane and 200 ml of methylene dichloride was charged. The reaction continued at 40° C. for 2 days. 25.6 grams of viscose liquid resin was collected, which had a RI of 1.5098.

Example 7

HEMA-based Monoimidazoliumbromide-dimethacrylate Resin (XJ8-54/FIG. 11) was prepared by a one-step condensation reaction from the imidazole precursor prepared as described in Example 3b. To a 250 ml 3-neck round flask, 60.2 g of HEMA-based monoimidazole-dimethacrylate resins (XJ8-48), 26.5 g of 1-bromooctane, 150 ml of methylene dichloride was charged. The reaction continued at 40° C. for 6 days. Finally 79 g of liquid resin was collected, which had a viscosity of 245 Pa·s at 20° C.

Example 8

HEMA-based Monoimidazoliumbromide-dimethacrylate Resin (XJ8-80/FIG. 10) was prepared by a one-step condensation reaction from the imidazole precursor prepared as described in Example 3b. To a 250 ml 3-neck round flask, 65.9 g of HEMA-based monoimidazole-dimethacrylate resins (XJ8-48) and 37.4 g of 1-bromododecane and 200 ml of methylene dichloride was charged. The reaction continued at 40° C. for 7 days. 99.5 grams of liquid resin was collected, which had a viscosity of 175 Pa·s at 20° C.

Example 9

Bis(3-dodecanylimidazoliumbromide)-Bisacrylate Resin (XJ8-152-1/FIG. 15) was prepared via a two-step one-pot process as described in the following: to a 250 ml 3-nech round flask, 72.5 g of pentaerythritol tetraacrylate (SR295) and 9.5 grams of imidazole, mixed at RT for 1 hr, then 9.4 grams of imidazole was added for addition 1 hr reaction prior to addition of another 9.6 grams of imidazole. It was mixed overnight at RT. Then set the flask into an oil-bath of 40° C. with addition of 95.2 grams of 1-bromododecane and continued for 7 days at 40° C. 221 grams of highly viscose resin was collected.

Example 10

Figure 16:
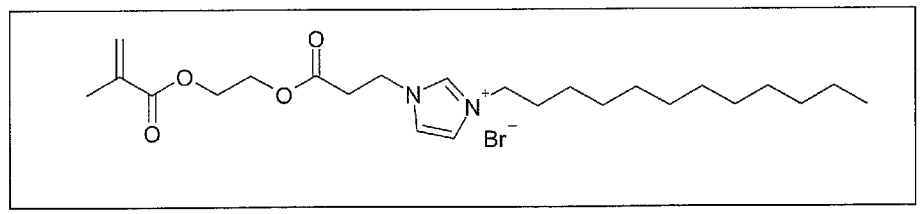
FIG. 16 depicts a 3-dodecanylimidazoliumbromide-monomethacrylate resin.

EGAMA-based monoimidazoliumbromide-monomethacrylate Resins (XJ8-160/FIG. 16) was prepared by a one-step condensation reaction from the imidazole precursor prepared as described in Example 3d. To a 250 ml 3-neck round flask, 127 grams of EGAMA-based monoimidazole-monomethacrylate resins (XJ8-157) and 124.0 grams of 1-bromododecane were charged. The reaction continued at 40° C. for 10 days. Finally 245 g of liquid resin was collected, which had a viscosity of 50 Pa·s at 20° C.

Example 11

AMAHP-based monosimidazolium-methacrylate Resin (XJ8-88/FIG. 11) was prepared via a one-step solution process as described in the following: to a 500 ml 3-nech round flask, 65.9 g of AMAHP-based monoimidazole-methacrylate resins (XJ8-81) and 28.8 of 1-bromooctane and 200 ml of methylene dichloride were charged. The reaction continued at 40° C. for 6 days. 61.3 grams of liquid resin was collected, which had a viscosity of 170 Pa·s at 20° C.

Example 12

AMAHP-based monosimidazolium-methacrylate Resin (X18-94/FIG. 11) was prepared via a one-step solution process as described in the following: to a 500 ml 3-nech round flask, 56.5 g of AMAHP-based monoimidazole-methacrylate resins (XJ8-85) and 33.1 of 1-bromoohaxane and 200 ml of methylene dichloride were charged. The reaction continued at 40° C. for 7 days. 80 grams of viscose liquid resin was collected, which had a viscosity of 410 Pa·s at 20° C.

Example 13

AMAHP-based monosimidazolium-methacrylate Resin (XJ8-88/FIG. 11) was prepared via a one-step solution process as described in the following: to a 500 ml 3-nech round flask, 43.0 of AMAHP-based monoimidazole-methacrylate resins (XJ8-111) and 25.0 of 1,12-dibromododecane and 150 ml of methylene dichloride were charged. The reaction continued at 40° C. for 3 days. 60 grams of highly viscose liquid resin was collected.

Example 14-15

Light curable flowable dental composites (IJ1-84-2 and IJ1-85-2) containing polymerizable imidazlium resin (XJ8-

Example 16-17

Light curable universal dental composites (XJ8-136 and XJ8-137) containing polymerizable imidazlium resin (XJ8-80 at 20.9-1.8% wt/wt) were formulated with 82% of filler, which demonstrated effective antibacterial activities and excellent mechanical properties without causing severe cytotoxicityas as showed in Table VI.

Example 18-21

Light curable universal dental composites (IJ1-115, 117, 118, and 137) containing polymerizable imidazlium resin (XJ8-80 at 0.9-1.8% wt/wt) were formulated with 82% of filler, which demonstrated effective antibacterial activities and excellent mechanical properties without causing severe cytotoxicityas showed in Table VIII.

Example 22-25

Light curable universal dental composites (IJ2-39, 40, 41, and 42) containing polymerizable imidazlium resin (XJ8-152 at 0.9-1.8% wt/wt) were formulated with 82% of filler, which demonstrated excellent mechanical properties as showed in Table X.

Example 26-29

Light curable universal dental composites (IJ2-189, 190, 191, and 192) containing polymerizable imidazlium resin (XJ8-160 at 0.9-1.8% wt/wt) were formulated with 82% of filler, which demonstrated effective antibacterial activities and excellent mechanical properties as showed in Table XII.

Example 30

Light curable universal dental composites (IJ2-205) containing polymerizable imidazlium resin(XJ8-88 at 1.8% wt/wt) were formulated with 82% of filler, which demonstrated effective antibacterial activities as showed in Table XIV.

Example 31

Light curable universal dental composites (IJ2-206) containing polymerizable imidazlium resin(XJ8-94 at 1.8% wt/wt) were formulated with 82% of filler, which demonstrated effective antibacterial activities as showed in Table XIV.

Example 32

Light curable universal dental composites (IJ2-207) containing polymerizable imidazlium resin(XJ8-54 at 1.8% wt/wt) were formulated with 82% of filler, which demonstrated effective antibacterial activities as showed in Table XIV.

Example 33

Light curable universal dental composites (IJ2-208) containing polymerizable imidazlium resin(XJ8-114 at 1.8% wt/wt) were formulated with 82% of filler, which demonstrated effective antibacterial activities as showed in Table XIV.

Comparative Example 1-2

Light curable universal dental composites (IJ1-138 and 139) were formulated with 82% of filler, which demonstrated excellent mechanical properties as showed in Table VIII.

Comparative Example 3

Light curable universal dental composites (IJ1-171) were formulated with 82% of filler, which demonstrated excellent mechanical properties as showed in Table XIV.

TABLE I

Compositions for Various Bisimidazole Dimethacrylate Resins

|  | Example 1 (XJ8-9) | Example 2 (XJ8-13) | Example 3a (XJ8-6) | Example 3b (XJ8-48) |
|---|---|---|---|---|
| Resin Composition | Isosorbide/ AMAHP/ TEGDMA | TCDC/ AMAHP/ TEGDMA | AMAHP/ HEMA | AMAHP/ HEMA |
| BIDMA Resin, TEGDMA, (wt/wt, %) | 90 10 | 90 10 | 100 0 | 100 0 |
| Resin Form | Liquid | liquid | Liquid | liquid |
| Viscosity @ 20° C. Pa·s | 690 | 40 | 3 | 40 |
| Solubility @ 37° C. in water | partially soluble | partially soluble | partially soluble | partially soluble |
| Solubility @ 37° C. in water/ethanol (50:50, w/w %) | soluble | soluble | soluble | soluble |

TABLE II

Compositions for Polymerizable Imidazolium-based Resins

|  | Example 4 (XJ8-45) | Example 5 (XJ8-31) | Example 6 (XJ8-40) | Example 7 (XJ8-54) |
|---|---|---|---|---|
| Imidazole-based Resin | XJ8-9 | XJ8-9 | XJ8-9 | XJ8-48 |
| Alkyl Bromide | C12 | C4 | C4 | C8 |
| Imidazolium-based Resin/ TEGDMA, (Wt/wt, %) | 100 0 | 80 20 | 100 0 | 100 0 |

TABLE II-continued

Compositions for Polymerizable Imidazolium-based Resins

|  | Example 4 (XJ8-45) | Example 5 (XJ8-31) | Example 6 (XJ8-40) | Example 7 (XJ8-54) |
|---|---|---|---|---|
| Resin Form | Liquid | Wax-like | Liquid | Liquid |
| Viscosity @ 20° C. Pa·s | 140 | N/A | 740 | 250 |
| Solubility @ 37° C. in EtOH | soluble | soluble | soluble | soluble |
| Solubility @ 37° C. in water/ethanol (50:50, w/w %) | soluble | soluble | soluble | soluble |
| Refractive Index @ 25° C. | N/A | 1.5130 ± 0.0007 | 1.5098 ± 0.0019 | N/A |

TABLE III

Compositions for Polymerizable Imidazolium-based Resins

|  | Example 8 (XJ8-80) | Example 9 (XJ8-152) | Example 10 (XJ8-160) |
|---|---|---|---|
| Imidazole-based Resin | XJ8-48 | XJ8-152-1 | XJ8-157 |
| Alkyl Bromide | C12 | C12 | C12 |
| Imidazolium-based Resin/ HEMA (Wt/wt, %) | 100 | 79 21 | 100 |
| Resin Form | Liquid | Liquid | Liquid |
| Viscosity @ 20° C. Pa·s | 175 | 50 | 50 |

TABLE IV

Compositions for Polymerizable Imidazolium-based Resins

|  | Example 11 (XJ8-88) | Example 12 (XJ8-94) | Example 14 (XJ8-114) |
|---|---|---|---|
| Imidazole-based Resin | XJ8-81 | XJ8-9 | XJ8-48 |
| Alkyl Bromide | C8 | C6 | 1,12-C12 |
| Imidazolium-based Resin/ TEGDMA, (Wt/wt, %) | 80 20 | 100 0 | 100 0 |
| Resin Form | Liquid | Liquid | Liquid |
| Viscosity @ 20° C. Pa·s | 170 | 410 | N/A |

TABLE V

Compositions of Formulated Resins and Composites

| Composition | XJ8-134 | XJ8-135 | XJ8-136 | XJ8-137 |
|---|---|---|---|---|
| Isosorbide-based Urethane Resin (999993/EBR10224) | 63% | 90% | 25.2% | 36.0% |
| TEGDMA (487170/110207) | 7% | 10% | 2.8% | 4.0% |
| Antibacterial Resin (XJ8-80) | 30% | 0% | 12.0% | 0% |
| Filler Blend (DP3-34) | 0% | 0% | 60.0% | 60.0% |
| CFU at Time zero |  |  | $1.27 \times 10^5$ | $1.27 \times 10^5$ |
| CFU at 24 hrs |  |  | <5 | $1.38 \times 10^5$ |
| Reduction, % |  |  | >99.999 | none |

TABLE VI

Compositions of Formulated Resins and Composites

| Composition |  | IJ1-138 | IJ1-84-2 | IJ1-85-2 | IJ1-118 | IJ1-137 |
|---|---|---|---|---|---|---|
| Isosorbide-based Urethane Resin (999993/EBR10224) |  | 90% | 32.4% | 34.2% | 14.6% | 15.4% |
| TEGDMA (487170/110207) |  | 10% | 3.6% | 3.8% | 1.6% | 1.7% |
| Antibacterial Resin (XJ8-80) |  | 0% | 4.0% | 2.0% | 1.8% | 0.9% |
| Filler Blend |  | 0% | 60.0% | 60.0% | 82.0% | 82.0% |
| Cytotoxicity (ISO Agarose Overlay) | Zone of Lysis(mm) | 0 | N/A | N/A | 0 | 0 |
|  | Grade | 0 | N/A | N/A | 2 | 1 |
|  | Reactivity | 0 | N/A | N/A | mild | slight |
| Antibacterial/S. aureus (ISO 22196) | CFU at 0 hr | $1.75 \times 10^5$ | $1.75 \times 10^5$ | $1.75 \times 10^5$ | $1.75 \times 10^5$ | $1.75 \times 10^5$ |
|  | CFU at 24 hrs (Reduction, %) | $2.10 \times 10^6$ | <5 >99.999 | <5 >99.999 | <5 >99.999 | 5 >99.999 |

TABLE VII

Cytotoxicity of Formulated Resins Containing Antibacterial Resin

| Resin Compositions | IJ1-107 | IJ1-109 | IJ1-108 | IJ1-110 | IJ1-112 (XJ8-135) | IJ1-111 |
|---|---|---|---|---|---|---|
| Isosorbide-based Urethane Resin (999993/EBR10224) | 81% | 81% | 85.5% | 85.5% | 90% | 90% |
| TEGDMA (487170/110207) | 9% | 9% | 9.5% | 9.5% | 10% | 10% |
| Antibacterial Resin(ABR)/(XJ8-80) | 10% | 10% | 5% | 5% | 0% | 0% |
| Agarose Overlay | N/A | Moderate | N/A | Moderate | N/A | Moderate |
| 1XMEM Elute | Severe | N/A | Mild | N/A | None | N/A |

TABLE VIII

Cytotoxicity, Antibacterial Activity and Mechanical Properties of Formulated Composites Containing Antibacterial Resin

| Composite Compositions | IJ1-115 | IJ1-118 | IJ1-117 | IJ1-137 | IJ1-139 | IJ1-138 |
|---|---|---|---|---|---|---|
| Resin Blend | IJ1-115 17.83% | IJ1-118 17.85% | IJ1-117 17.75% | IJ1-137 17.81% | IJ1-112 17.84% | IJ1-111 17.93% |
| Filler Blend (XJ8-148) | 82.17% | 82.15% | 82.25% | 82.19% | 82.16% | 82.07% |
| Antibacterial Resin(ABR) (XJ8-80) | 1.78% | 1.78% | 0.89% | 0.89% | 0% | 0% |
| Compr. St. (MPa) | 322 ± 12 | 310 ± 12 | 330 ± 14 | 318 ± 8 | 339 ± 10 | 353 ± 9 |
| Compr. Mod. (MPa) | 6570 ± 150 | 6530 ± 230 | 6530 ± 100 | 6390 ± 330 | 6410 ± 40 | 6320 ± 380 |
| Flex. St. (MPa) | 99 ± 6 | 97 ± 6 | 114 ± 8 | 120 ± 13 | 119 ± 9 | 106 ± 8 |
| Flex. Mod. (MPa | 8070 ± 640 | 9190 ± 940 | 9080 ± 670 | 10330 ± 1330 | 10600 ± 1310 | 11320 ± 1390 |
| Agarose Overlay | N/A | Mild | N/A | Slight | N/A | None |
| 1XMEM Elute | Slight | N/A | Slight | N/A | None | N/A |
| Antibacterial Activity Vs S. aurues 24 hrs/CFU Reduction, % | N/A | $1.75 \times 10^5$ <5 >99.999 | N/A | $1.75 \times 10^5$ 5 99.999 | N/A | $1.75 \times 10^5$ $2.10 \times 10^6$ None |

TABLE IX

Mechanical Properties of Formulated Resins Containing Antibacterial Resin

| Resin Compositions | IJ1-206 | IJ1-208 | IJ1-207 | IJ2-1 | IJ1-112 (XJ8-135) | IJ1-111 |
|---|---|---|---|---|---|---|
| Isosorbide-based Urethane Resin (999993/EBR10224) | 81% | 81% | 85.5% | 85.5% | 90% | 90% |
| TEGDMA (487170/110207) | 9% | 9% | 9.5% | 9.5% | 10% | 10% |
| Antibacterial Resin(ABR)/(XJ8-152) | 10% | 10% | 5% | 5% | 0% | 0% |
| CQ | 0.165% | 0.165% | 0.165% | 0.165% | 0.165% | 0.165% |
| EDAB | 0.300% | 0% | 0.300% | 0% | 0.300% | 0% |
| LTPO | 0% | 0.40% | 0% | 0.40% | 0% | 0.40% |
| BHT | 0.030% | 0.030% | 0.030% | 0.030% | 0.030% | 0.030% |
| Viscosity@20° C. Pa·s | 35 | 35 | 40 | 40 | 40 | 35 |
| Compr. Mod. (MPa) | 2530 ± 40 | 2550 ± 50 | 2620 ± 60 | 2640 ± 100 | 2640 ± 40 | 2680 ± 40 |
| Flex. St. (MPa) | 68 ± 3 | 92 ± 2 | 74 ± 3 | 89 ± 3 | 80 ± 2 | 94 ± 2 |
| Flex. Mod. (MPa | 1740 ± 140 | 2430 ± 110 | 1680 ± 120 | 2160 ± 130 | 1850 ± 100 | 2190 ± 130 |

TABLE X

Mechanical Properties of Formulated Composites Containing Antibacterial Resin

| Composite Compositions | IJ2-39 | IJ2-41 | IJ2-40 | IJ2-42 | IJ1-139 | IJ1-138 |
|---|---|---|---|---|---|---|
| Resin Blend | IJ1-206 | IJ1-208 | IJ1-207 | IJ2-1 | IJ1-112 | IJ1-111 |
|  | 18.63% | 18.31% | 18.27% | 18.57% | 17.84% | 17.93% |
| Filler Blend (XJ8-148) | 81.37% | 81.69% | 81.76% | 81.43% | 82.16% | 82.07% |
| Antibacterial Resin(ABR) (XJ8-152) | 1.86% | 1.83% | 0.92% | 0.93% | 0% | 0% |
| Compr. St. (MPa) | 300 ± 6 | 296 ± 20 | 313 ± 10 | 324 ± 12 | 339 ± 10 | 353 ± 9 |
| Compr. Mod. (MPa) | 6300 ± 40 | 6250 ± 230 | 6450 ± 150 | 6570 ± 160 | 6410 ± 40 | 6320 ± 380 |
| Flex. St. (MPa) | 108 ± 8 | 115 ± 6 | 114 ± 8 | 120 ± 8 | 119 ± 9 | 106 ± 8 |
| Flex. Mod. (MPa | 9800 ± 340 | 9910 ± 490 | 8790 ± 660 | 10800 ± 780 | 10600 ± 1310 | 11320 ± 1390 |

TABLE XI

Mechanical Properties of Formulated Resins Containing Antibacterial Resin

| Resin Compositions | IJ2-178 | IJ2-180 | IJ2-179 | IJ2-181 | IJ2-131 | IJ2-132 |
|---|---|---|---|---|---|---|
| Isosorbide-based Urethane Resin (999993/EBR10224) | 81% | 81% | 85.5% | 85.5% | 90% | 90% |
| TEGDMA (487170/110207) | 9% | 9% | 9.5% | 9.5% | 10% | 10% |
| Antibacterial Resin(ABR) (XJ8-160) | 10% | 10% | 5% | 5% | 0% | 0% |
| CQ | 0.165% | 0.165% | 0.165% | 0.165% | 0.165% | 0% |
| EDAB | 0.300% | 0% | 0.300% | 0% | 0% | 0% |
| LTPO | 0% | 0.40% | 0% | 0.40% | 0% | 0.40% |
| BHT | 0.030% | 0.030% | 0.030% | 0.030% | 0.030% | 0.030% |
| Viscosity@20° C. Pa·s | 35 | 35 | 35 | 35 | 40 | 40 |
| Compr. St. (MPa) | 2500 ± 30 | 2440 ± 00 | 2290 ± 40 | 2580 ± 40 | N/A | 2640 ± 30 |
| Compr. Mod. (MPa) |  |  |  |  |  |  |
| Flex. St. (MPa) | 63 ± 6 | 77 ± 5 | 70 ± 4 | 82 ± 5 | N/A | 97 ± 1 |
| Flex. Mod. (MPa | 1560 ± 210 | 1850 ± 250 | 1690 ± 200 | 1850 ± 220 | N/A | 2280 ± 60 |

TABLE XII

Properties of Formulated Composites Containing Antibacterial Resin

| Composite Compositions | IJ2-189 | IJ2-191 | IJ2-190 | IJ2-192 | IJ2-170 | IJ2-171 |
|---|---|---|---|---|---|---|
| Resin Blend | IJ2-178 | IJ2-180 | IJ2-179 | IJ2-181 | IJ2-131 | IJ2-132 |
|  | 17.52% | 17.43% | 17.57% | 17.22% | 17.48% | 17.76% |
| Filler Blend (XJ8-148) | 82.48% | 82.57% | 82.43% | 82.78% | 82.52% | 82.24% |
| Antibacterial Resin(ABR) (XJ8-160) | 1.75% | 1.74% | 0.88% | 0.86% | 0% | 0% |
| Compr. St. (MPa) | 322 ± 11 | 313 ± 9 | 328 ± 14 | 339 ± 12 | 295 ± 13 | 332 ± 16 |
| Compr. Mod. (MPa) | 6350 ± 90 | 6520 ± 120 | 6140 ± 180 | 6610 ± 90 | 5690 ± 120 | 6350 ± 120 |
| Flex. St. (MPa) | 121 ± 3 | 138 ± 13 | 129 ± 13 | 136 ± 8 | 96 ± 8 | 118 ± 16 |
| Flex. Mod. (MPa | 9390 ± 610 | 11800 ± 690 | 10850 ± 1130 | 12320 ± 660 | 6720 ± 650 | 10840 ± 1170 |
| Antibacterial Activity | $1.65 \times 10^5$ | $1.65 \times 10^5$ | $1.65 \times 10^5$ | $1.65 \times 10^5$ |  | $1.65 \times 10^5$ |
| Vs S. aurues | 5 | <5 | <5 | <5 | N/A | $1.85 \times 10^4$ |
| 24 hrs/CFU Reduction, % | 99.973 | >99.973 | >99.973 | >99.973 |  | N/A |

TABLE XIII

Compositions of Formulated Resins Containing Different Antibacterial Resins

| Resin Compositions | IJ2-201 | IJ12-202 | IJ2-203 | IJ2-204 | IJ2-132 |
|---|---|---|---|---|---|
| Isosorbide-based Urethane Resin (999993/EBR10224) | 81% | 81% | 81% | 81% | 90% |
| TEGDMA (487170/110207) | 9% | 9% | 9% | 9% | 10% |
| Antibacterial Resin (ABR) | | | | | |
| XJ8-88 | 10% | | | | 0% |
| XJ8-94 | | 10% | | | |
| XJ8-54 | | | 10% | | |
| XJ8-114 | | | | 10% | |
| CQ | 0.165% | 0.165% | 0.165% | 0.165% | 0% |
| EDAB | 0% | 0% | 0% | 0% | 0% |
| LTPO | 0.40% | 0.40% | 0.40% | 0.40% | 0.40% |
| BHT | 0.030% | 0.030% | 0.030% | 0.030% | 0.030% |
| Viscosity@20° C. Pa·s | 40 | 40 | 40 | 40 | 40 |
| Compr. St. (MPa) | 2460 ± 30 | 2490 ± 70 | 2480 ± 50 | N/A | 2640 ± 30 |
| Compr. Mod. (MPa) | | | | | |
| Flex. St. (MPa) | 80 ± 2 | 86 ± 3 | 86 ± 3 | N/A | 97 ± 1 |
| Flex. Mod. (MPa | 2030 ± 100 | 2330 ± 120 | 2210 ± 150 | N/A | 2280 ± 60 |

TABLE XIV

Antibacterial Activities and Properties of Formulated Composites Containing Antibacterial Resin

| Composite Compositions | IJ2-205 | IJ2-206 | IJ2-207 | IJ2-208 | IJ2-171 |
|---|---|---|---|---|---|
| Resin Blend | IJ2-201 | IJ2-202 | IJ2-203 | IJ2-204 | IJ2-132 |
|  | 18.18% | 18.23% | 18..02% | 18.57% | 17.76% |
| Filler Blend (XJ8-148) | 81.83% | 81.77% | 81.98% | 81.43% | 82.24% |
| Antibacterial Resins (ABR) | 1.82% | 1.82% | 1.80% | 1.86% | 0% |
| Compr. St. (MPa) | 335 ± 11 | 325 ± 14 | 328 ± 8 | 340 ± 15 | 332 ± 16 |
| Compr. Mod. (MPa) | 6620 ± 80 | 6520 ± 120 | 6560 ± 180 | 6380 ± 220 | 6350 ± 120 |
| Flex. St. (MPa) | 148 ± 11 | 146 ± 11 | 149 ± 7 | 147 ± 13 | 118 ± 16 |
| Flex. Mod. (MPa | 13840 ± 410 | 13390 ± 1390 | 11900 ± 880 | 11350 ± 1140 | 10840 ± 1170 |
| Antibacterial Activity Vs S. aurues | $2.05 \times 10^5$ 5 | $2.05 \times 10^5$ $1.40 \times 10^2$ | $2.05 \times 10^5$ <5 | $2.05 \times 10^5$ $1.84 \times 10^3$ | $2.05 \times 10^5$ $2.40 \times 10^5$ |
| 24 hrs/CFU Reduction, % | 99.998 | 99.942 | >99.973 | 99.233 | N/A |

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What I claim is:

1. A dental composition comprising:
   from about 0.1 weight percent to about 5.0 weight percent of an imidazolium-based polymerizable resin;
   from about 5 weight percent to about 60 weight percent of a non-imidazolium-based polymerizable resin;
   from about 0.005 weight percent to about 5 weight percent of at least one of a photoinitiator, a thermal/redox initiator or other additive;
   from about 40 weight percent to about 90 weight percent of a glass filler having a particle size of from about 10 nm to about 100 microns; and
   an optional inert solvent wherein the imidazolium-based polymerizable resin has a formula of:

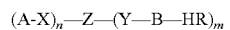

$(A-X)_n-Z-(Y-B-HR)_m$ wherein A is a polymerizable moiety selected from the group consisting of methacrylate, acrylate, epoxy and vinylether,
   wherein B is an imidazole or a methyl imidazole,
   wherein R is a hydrogen atom or an alky group having from 1 to 22 carbon atoms,
   wherein H is a halogen atom, a chlorine atom, a bromine atom or an iodine atom,
   wherein X and Y are the same or different and are an ether, ester, amide, imide, direct link, alkyl, or aromatic,
   wherein Z is an alkyl or an aromatic, and
   wherein n and m are integers of at least 1.

2. The dental composition according to claim 1, wherein the imidazolium-based polymerizable resin demonstrates antibacterial activity capable of killing at least 99 percent of S. mutans.

3. The dental composition according to claim 1, wherein the dental composition in its entirety is capable of an antibacterial activity capable to killing more than 99 percent of *S. mutans* and *S. aureus*.

* * * * *